United States Patent [19]

Easterly et al.

[11] Patent Number: 5,597,729
[45] Date of Patent: Jan. 28, 1997

[54] METHOD FOR THE REMOVAL AND RECOVERY OF MERCURY

[75] Inventors: Clay E. Easterly, Knoxville; Arpad A. Vass, Oak Ridge; Richard L. Tyndall, Clinton, all of Tenn.

[73] Assignee: Martin Marietta Energy Systems, Inc., Oak Ridge, Tenn.

[21] Appl. No.: 422,028

[22] Filed: Apr. 13, 1995

[51] Int. Cl.⁶ ................................. B09C 1/02; B09C 1/10
[52] U.S. Cl. .................. 435/262.5; 588/232; 588/236
[58] Field of Search .................. 435/262.5; 588/232, 588/236

[56] References Cited

U.S. PATENT DOCUMENTS 5,314,821  5/1994  Tyndall ........................... 435/252.1
5,420,035  5/1995  Tyndall ........................... 435/252.1
5,449,618  9/1995  Tyndall et al. .................. 435/262.5

*Primary Examiner*—Esther Kepplinger
*Assistant Examiner*—Curtis E. Sherrer
*Attorney, Agent, or Firm*—Shelley L. Stafford; Harold W. Adams

[57] ABSTRACT

The present invention is an enhanced method for the removal and recovery of mercury from mercury-contaminated matrices. The method involves contacting a mercury-contaminated matrix with an aqueous dispersant solution derived from specific intra-amoebic isolates to release the mercury from the mercury-contaminated matrix and emulsify the mercury; then, contacting the matrix with an amalgamating metal from a metal source to amalgamate the mercury to the amalgamating metal; removing the metallic source from the mercury-contaminated matrix; and heating the metallic source to vaporize the mercury in a closed system to capture the mercury vapors.

19 Claims, No Drawings

5,597,729

METHOD FOR THE REMOVAL AND RECOVERY OF MERCURY

This invention was made with Government support under contract DE-AC05-OR21400 awarded by the U.S. Department of Energy to Martin Marietta Energy Systems, Inc., and the Government has certain rights in this invention.

FIELD OF THE INVENTION

The present invention relates to methods for the removal and recovery of mercury from mercury-contaminated matrices, and more particularly to methods which utilize by-products of intra-amoebic isolates.

BACKGROUND OF THE INVENTION

Contamination of soil with mercury is a real problem in areas near weapons manufacturing sites since mercury was a key element used in production. As a result of work in support of weapons development, many metric tons of mercury were lost to the environment. Mercury contamination of soil is widespread around these sites, extending into residential areas. Cleanup efforts at these sites have been conducted for some time using a method that is both expensive and cumbersome. One method involves heating the soil in a retort and capturing the mercury from the vapor state. Another method involves excavating the contaminated soil and placing it into drums for storage at an approved hazardous waste site.

Mercury contaminated-soil exists not only at government weapons manufacturing sites, but at other industrial sites as well. The problem of mercury recovery and removal is widespread. Therefore, there is a need for alternative methods for the remediation of mercury-contaminated soil.

OBJECTS OF THE INVENTION

Accordingly, it is an object of the present invention to provide a new and improved method for the removal of mercury from mercury-contaminated matrices.

It is another object of the present invention to provide a new and improved method for the removal and recovery of mercury from mercury-contaminated matrices.

It is yet another object of the present invention to provide a new and improved method for the removal and recovery of mercury from mercury-contaminated soils.

Further and other objects of the present invention will become apparent from the description contained herein.

SUMMARY

In accordance with one aspect of the present invention, the foregoing and other objects are achieved by a method for the removal of mercury from mercury-contaminated matrices comprising the steps of: deriving an aqueous dispersant solution from a culture of a bacterium comprising an intra-amoebic isolate possessing all the identifying characteristics of American Type Culture Collection Deposit Number 75529, a mutant of the isolate possessing all the identifying characteristics thereof, or mixtures thereof. Then, rinsing a mercury-contaminated matrix with a sufficient amount of the aqueous dispersant solution to release the mercury from the mercury-contaminated matrix.

In accordance with another aspect of the present invention, a method for the removal of mercury from mercury-contaminated matrices comprises the steps of: deriving an aqueous dispersant solution from a culture of a bacterium comprising an intra-amoebic isolate possessing all the identifying characteristics of American Type Culture Collection Deposit Number 75529, a mutant of the isolate possessing all the identifying characteristics thereof, or mixtures thereof. Then, contacting a mercury-contaminated matrix with a sufficient amount of the aqueous dispersant solution to release the mercury from the mercury-contaminated matrix and emulsify the mercury; contacting the mercury-contaminated matrix with a sufficient amount of an amalgamating metal from a metal source to amalgamate the mercury to the metal; and removing the metallic source from the mercury-contaminated matrix.

In accordance with a further aspect of the present invention, a method for the removal and recovery of mercury from mercury-contaminated matrices comprises the steps of: deriving an aqueous dispersant solution from a culture of a bacterium comprising an intra-amoebic isolate possessing all the identifying characteristics of American Type Culture Collection Deposit Number 75529, a mutant of the isolate possessing all the identifying characteristics thereof, or mixtures thereof. Then, contacting a mercury-contaminated matrix with a sufficient amount of the aqueous dispersant solution to release the mercury from the mercury-contaminated matrix and emulsify the mercury; contacting the mercury-contaminated matrix with a sufficient amount of an amalgamating metal from a metal source to amalgamate the mercury to the metal; removing the metallic source from the mercury-contaminated matrix; and heating the metallic source in a closed system to capture the mercury from the metal.

DETAILED DESCRIPTION OF THE INVENTION

This application incorporates herein by reference, the entire disclosure of U.S. Pat. No. 5,314,821, issued May 24, 1994 and the entire disclosure of application Ser. No. 08/168,603, filed Dec. 16, 1993, entitled *Methods of Degrading Napalm B,* of which the issue fee has been paid U.S. Pat. No. 5,449,618, issued Sep. 12, 1995.

Amoebae, isolated from soils and well water contaminated with toxic wastes, harbor bacteria, many of which possess unusual characteristics. These include the ability to degrade agar, the utilization of methane as a sole carbon source, the production of biogenic crystals and powerful biodispersants and the ability to degrade a number of toxins.

Amoeba/bacteria consortium 46, ATCC Deposit Reference No. 40908, was found to contain certain useful bacteria, designated as intra-amoebic isolates 13, NAP-1, 1S and CR-1. Isolate 1S was found to produce a compound or biodispersant, which when released into a medium during log growth of the bacteria, elicited a dispersion effect. This biodispersant was more effective after autoclaving and resultant sterilization. Preliminary work with column chromatography and concentration procedures using Amicon filters, showed that the biodispersant possesses a negative charge associated with at least part of the molecule. The molecule apparently comprises denatured protein, carbohydrate, and lipid since lipase and trypsin significantly reduced its effectiveness. The biodispersant is able to disperse or emulsify complex polymers into microdroplets and when tested by a tensiometer was shown to have marked ability to reduce surface tension. This ability is so pronounced that when biodispersant is added to elemental mercury, the surface tension between the mercury molecules is disrupted, resulting in a microemulsion of mercury. Similarly, the surface tension reducing capability of the biodispersant can disrupt the ionic and covalent bonds between particles of a matrix, such as soil, destroying or dispersing the particles. In soil, for example, the biodispersant disrupts soil particles such that soil fines are dispersed or destroyed, forming an emulsion. The soil also becomes emulsified on exposure to the biodispersant. Thus, addition of the biodispersant to mercury-contaminated soil results in a concomitant dispersion of the soil fines, desorption or release of the mercury from the soil fines, therefore allowing for the amalgamation of the mercury to an appropriate amalgamating material from an appropriate material source, such as metal, preferably copper alloys like copper/zinc or copper/iron alloys.

These bacterially-produced biodispersants can be used to not only destroy soil fines, but other matrices as well. They can emulsify a variety of compounds including inorganic substances, such as metals (e.g., mercury), and hence facilitate the desorption or release of the contaminating compound from the matrix of which the compound is contaminating. Once the compound is released or desorbed from the matrix, it can then be removed. One way to remove the contaminating compound or substance is through amalgamation, allowing the contaminating substance to amalgamate to the appropriate material, such as metal. Then a magnet is used to extract the amalgamation. If a magnet is to be used as the means for removing or extracting the amalgamation from the emulsion, then an amalgamating material possessing magnetic properties is needed. For instance, upon the addition of the biodispersant to mercury-contaminated soil, the soil fines are destroyed, releasing the mercury from the soil matrix to form an emulsion. Then, the mercury is removed by amalgamation to copper and the copper source is extracted from the emulsion with a magnet. One further step recovers the mercury from the copper source by means of a distillation process wherein the amalgamation is heated to a temperature sufficient to vaporize the mercury. The boiling point of mercury is 356.73° C. This heating process is performed within a closed system, such as a vacuum oven, in order to capture the mercury vapors and prevent any release to the environment.

EXAMPLE I

A dispersant was derived from Isolate 1S as described hereinabove, incorporated by reference. Twenty grams of soil, with stones removed, was spiked with 0.3 ml of elemental mercury and placed in four 50 cc centrifuge tubes such that each tube contained 20 grams of mercury-spiked soil. They were then mixed for 24 hours. BB's (copper coated) were added to each tube of spiked soil. Forty milliliters of water was added to one set of tubes as the control and forty milliliters of the 10% biodispersant solution was added to the second set of tubes. One set of tubes was placed on a rotating shaker and the second set of tubes was not shaken. After 24 hours, the BB's were removed and examined for amalgamation of mercury to the copper.

EXAMPLE II

A dispersant was derived from Isolate 1S as described hereinabove, incorporated by reference. Twenty grams of soil, with stones removed, was spiked with 0.3 ml of elemental mercury and placed in four 50 cc centrifuge tubes such that each tube contained 20 grams of mercury-spiked soil. They were then mixed for 24 hours. U.S. pennies were added to each tube of spiked soil. Forty milliliters of water was added to one set of tubes as the control and forty milliliters of the 10% biodispersant solution was added to the second set of tubes. One set of tubes was placed on a rotating shaker and the second set of tubes was not shaken. After 24 hours, the pennies were removed and examined for amalgamation of mercury to the copper.

The method of removing and recovering contaminating compounds or substances, such as an inorganic substance, from a matrix requires a matrix sample to be of sufficient amount. A sufficient amount of matrix is that amount containing a detectable amount of contaminating compound or substance.

It was observed during the course of the experimental work that when the biodispersant solution was added to the mercury-spiked samples a visible mercury layer formed on top of the soil particles, indicating the mercury was no longer bound to the soil particles. The soil samples that were left untreated with the biodispersant solution showed no such change.

TABLE 1

Ability of Mercury to Amalgamate to Various Types of Copper

| Sol'n | Type of Copper | Copper in Water | Copper in 10% Biodispersant |
|---|---|---|---|
| | BB's | Slow | Rapid |
| | Pennies | Slow | Rapid |

Table 1 shows initial experiments undertaken to determine the ability of mercury to amalgamate to types of copper in a liquid matrix (distilled water or 10% biodispersant in distilled water). Mercury amalgamated to both BB's and pennies in less than 24 hours.

The experiments using pennies were very successful. Pennies have a thick coating of copper encasing an alloy of 2.7% copper and 97.3% zinc. Penny surrogates could be developed with an iron core, enabling them to be removed from the emulsified soil slurry with a magnet. The results showed that mercury was solidly amalgamated to pennies in less than 24 hours from the soil tubes containing the biodispersant in both the shaken and not shaken sample sets, in the above example. Similar results were obtained when this experiment was repeated without removing stones from the soil matrix.

TABLE 2

Enhanced Ability of Mercury to Amalgamate to Copper

| Element | Control Penny | Spiked-BD | Spiked + BD |
|---|---|---|---|
| Al | 0.9 | 0.4 | 0.7 |
| Ca | — | — | — |
| Cl | 0.3 | — | — |
| Cu | 74.7 | 63.1 | 22.3 |
| Fe | — | 0.4 | — |
| Hg | — | 15.6 | 61.1 |
| K | trace | — | — |
| Mg | — | — | — |
| S | — | — | — |
| Si | 0.3 | 0.6 | 1.1 |
| Zn | 3.0 | 2.0 | 2.0 |

Table 2 demonstrates in percent by weight of materials on the surface of the pennies analyzed by energy dispersive x-ray. The experiments followed the same procedure given in the examples. One set of centrifuge tubes contained mercury-spiked soil without the biodispersant solution (–BD) with the penny added and one set of tubes contained mercury-spiked soil with the biodispersant solution (+BD) with the penny added. The control penny was not treated in any way. It is known in the art that mercury will amalgamate to copper without any additives. Table 2 shows this clearly in the set of results obtained from the mercury-spiked soil without any biodispersant added. But, the results also show an increase in the percentage of mercury on the surface of the penny when the biodispersant was added, causing the copper value to decrease as mercury covers the penny's copper surface. This demonstrates a significant enhancement of the ability of elemental mercury to amalgamate to copper in the presence of the biodispersant.

Biodispersants are crucial to this process. They allow for the desorption and liberation of elemental mercury from soil. Without biodispersant, mercury seems to have a greater affinity for soil than copper, and little amalgamation occurs. Additional studies using metal piping which was contaminated with mercury showed that rinsing the pipes in a biodispersant solution removed a greater amount of mercury than washing the pipe in water or even detergent solution.

DEPOSIT OF MICROORGANISMS

The applicants, in accordance with the provisions of the Budapest treaty on the international recognition of the deposit of microorganisms for the purposes of patent procedure under the Budapest Treaty, did deposit samples of Isolate NAP-1, Isolate 13, Isolate CR-1. and Isolate 1S with the American Type Culture Collection (ATCC), 12301 Parklawn Drive, Rockville, Mass. 20852, U.S.A. on Aug. 20, 1993 and assigned ATCC deposit reference Numbers 77526, 77527, 77528, and 77529, respectively. Each culture is hereby irrevocably and without restriction or condition released to the public upon the issuance of letters patent herefor.

What is claimed is:

1. A method for the removal of mercury from mercury-contaminated matrices comprising the steps of:
    a. providing a culture of a bacterium comprising an intra-amoebic isolate possessing all the identifying characteristics of American Type Culture Collection Deposit Number 75529, a mutant of said isolate possessing all the identifying characteristics thereof, or mixtures thereof;
    b. deriving an aqueous dispersant solution from said culture;
    c. rinsing a mercury-contaminated matrix with a sufficient amount of said aqueous dispersant solution to release said mercury from said mercury-contaminated matrix.

2. The method for the recovery and removal of mercury from mercury-contaminated matrices in accordance with claim 1 wherein said dispersant solution is diluted 1:10 with water after step b.

3. A method for the removal of mercury from mercury-contaminated matrices comprising the steps of:
    a. providing a culture of a bacterium comprising an intra-amoebic isolate possessing all the identifying characteristics of American Type Culture Collection Deposit Number 75529, a mutant of said isolate possessing all the identifying characteristics thereof, or mixtures thereof;
    b. deriving an aqueous dispersant solution from said culture;
    c. contacting a mercury-contaminated matrix with a sufficient amount of said aqueous dispersant solution to release said mercury from said mercury-contaminated matrix and emulsify said mercury;
    d. providing an amalgamating metal from a metallic source;
    e. contacting said mercury-contaminated matrix with a sufficient amount of said amalgamating metal from said metallic source to amalgamate said mercury to said amalgamating metal; and
    f. removing said metallic source with the amalgamated mercury from said mercury-contaminated matrix.

4. The method for the removal of mercury from mercury-contaminated matrices in accordance with claim 3 wherein said dispersant solution is diluted 1:10 with water after step b.

5. The method for the removal of mercury from mercury-contaminated matrices in accordance with claim 3 wherein said metallic source is a copper source and said amalgamating metal is copper.

6. The method for the removal of mercury from mercury-contaminated matrices in accordance with claim 5 wherein said copper source comprises a copper/zinc alloy.

7. The method for the removal of mercury from mercury-contaminated matrices in accordance with claim 5 wherein said copper source comprises a coating of copper encasing an alloy of 2.7% copper and 97.3% zinc.

8. The method for the removal of mercury from mercury-contaminated matrices in accordance with claim 5 wherein said copper source comprises a coating of copper encasing an iron core.

9. The method for the removal of mercury from mercury-contaminated matrices in accordance with claim 3 wherein said copper source is removed by a magnet.

10. A method for the removal and recovery of mercury from mercury-contaminated matrices comprising the steps of:
    a. providing a culture of a bacterium comprising an intra-amoebic isolate possessing all the identifying characteristics of American Type Culture Collection Deposit Number 75529, a mutant of said isolate possessing all the identifying characteristics thereof, or mixtures thereof;
    b. deriving an aqueous dispersant solution from said culture;
    c. contacting a mercury-contaminated matrix with a sufficient amount of said aqueous dispersant solution to release said mercury from said mercury-contaminated matrix and emulsify said mercury;
    d. providing an amalgamating metal from a metallic source;
    e. contacting said mercury-contaminated matrix with a sufficient amount of said amalgamating metal from said metallic source to amalgamate said mercury to said amalgamating metal;
    f. removing said metallic source with the amalgamated mercury from said matrix; and
    g. heating said metallic source to a temperature sufficient to distill said mercury.

11. The method for the removal and recovery of mercury from mercury-contaminated matrices in accordance with claim 10 wherein said dispersant solution is diluted 1:10 with water after step b.

12. The method for the removal and recovery of mercury from mercury-contaminated matrices in accordance with claim 10 wherein said metallic source comprises copper and said amalgamating metal comprises copper.

13. The method for the removal and recovery of mercury from mercury-contaminated matrices in accordance with claim 12 wherein said copper source comprises a copper/zinc alloy.

14. The method for the removal and recovery of mercury from mercury-contaminated matrices in accordance with claim 12 wherein said copper source comprises a coating of copper encasing an alloy of 2.7% copper and 97.3% zinc.

15. The method for the removal and recovery of mercury from mercury-contaminated matrices in accordance with claim 12 wherein said copper source comprises a coating of copper encasing an iron core.

16. The method for the removal and recovery of mercury from mercury-contaminated matrices in accordance with claim 10 wherein said metallic source is removed by a magnet.

17. The method for the removal and recovery of mercury from mercury-contaminated matrices in accordance with claim 10 wherein said heating step occurs in a closed system to capture said mercury upon vaporization.

18. The method for the removal and recovery of mercury from mercury-contaminated matrices in accordance with claim 17 wherein said closed system is a vacuum oven.

19. The method for the removal and recovery of mercury from mercury-contaminated matrices in accordance with claim 10 wherein said mercury-contaminated matrix is soil.

* * * * *